(12) United States Patent
Glazer et al.

(10) Patent No.: US 6,740,507 B2
(45) Date of Patent: May 25, 2004

(54) ENGINEERING OF LIVING CELLS FOR THE EXPRESSION OF HOLO-PHYCOBILIPROTEIN-BASED CONSTRUCTS

(75) Inventors: Alexander N. Glazer, Berkeley, CA (US); Aaron J. Tooley, Berkeley, CA (US); Yuping Cai, Carmel, IN (US)

(73) Assignee: The Regents of the University of California, Oakland, CA (US)

( * ) Notice: Subject to any disclaimer, the term of this patent is extended or adjusted under 35 U.S.C. 154(b) by 108 days.

(21) Appl. No.: 09/919,486

(22) Filed: Jul. 31, 2001

(65) Prior Publication Data

US 2003/0027285 A1 Feb. 6, 2003

(51) Int. Cl.[7] .................................................. C12P 21/04
(52) U.S. Cl. ..................... 435/70.1; 435/70.1; 435/325; 435/252.3; 435/252.2; 435/455; 435/468; 435/449; 435/419; 435/7.92; 435/320.1; 435/6
(58) Field of Search .................. 435/6, 320.1, 325, 435/70.1, 252.3, 252.2, 455, 468, 449, 419, 792

(56) References Cited

U.S. PATENT DOCUMENTS

2001/0055783 A1 * 12/2001 Allnutt et al. ............. 435/7.92

OTHER PUBLICATIONS

Fairchild et al., PNAS, vol. 89, pp. 7017–7021, 1992.*
Frankenberg et al., The Plant Cell, vol. 13, pp. 965–978, Apr. 2001.*
Tooley et al., PNAS, vol. 98, No. 19, pp. 10560–10565, Sep. 2001.*
Landgraf et al., FEBS Letters, vol. 508, pp. 459–462, 2001.*
Allnutt et al. US 2001/055783, Dec. 27, 2001.
Gambetta G.A. et al. PNAS USA 98(19):10566–71, Sep. 11, 2001.
Frankenberg N. et al. Plant Cell 13(4):965–78, Apr. 2001.
Kronick M.N. et al. J. Immunol. Methods 92:1–13, Aug. 1986.
Fairchild C.D. et al. J. Biol. Chem. 269(12):8686–94, Mar. 25, 1994.

* cited by examiner

Primary Examiner—Karen Cochrane Carlson
Assistant Examiner—Hope A. Robinson
(74) Attorney, Agent, or Firm—Richard Aron Osman

(57) ABSTRACT

Recombinant cells which express a fluorescent holo-phycobiliprotein fusion protein and methods of use are described. The cells comprises a bilin, a recombinant bilin reductase, an apo-phycobiliprotein fusion protein precursor of the fusion protein comprising a corresponding apo-phycobiliprotein domain, and a recombinant phycobiliprotein domain-bilin lyase, which components react to form the holo-phycobiliprotein fusion protein. Also described are holo-phycobiliprotein based transcription reporter cells and assays, which cells conditionally express a heterologous-to-the-cell, fluorescent, first holo-phycobiliprotein domain.

17 Claims, 3 Drawing Sheets

ENGINEERING OF LIVING CELLS FOR THE EXPRESSION OF HOLO-PHYCOBILIPROTEIN-BASED CONSTRUCTS

This invention was made with Government support under contract DE-FG-9161125 awarded by the U.S. Department of Energy. The Government has certain rights in this invention.

INTRODUCTION

1. Field of the Invention

The field of the invention is recombinant cells engineered to express heterologous holo-phycobiliproteins.

2. Background of the Invention

The phycobiliproteins are a family of light-harvesting proteins found in cyanobacteria, red algae, and the cryptomonads. These proteins absorb strongly in the visible region of the spectrum because they carry various covalently attached linear tetrapyrrole prosthetic groups (bilins). Phycobiliproteins are tightly associated αβ heterodimers, in which each subunit carries bilin(s) thioether-linked to particular cysteinyl residues (1–3).

Steps involved in bilin biosynthesis and bilin addition to apophycobiliprotein subunits have been inferred from diverse studies (e.g., 4–6). However, the entire pathway from heme to a particular holophycobiliprotein subunit has not hitherto been reconstituted either in vitro or in vivo. This achievement is reported here.

The invention offers numerous applications in the enzymology and chemistry of phycobiliprotein synthesis, and enables the use of phycobiliproteins as in vivo fluorescent protein probes. Purified native phycobiliproteins and their subunits fluoresce strongly and, since 1982, have been widely used as external labels for cell sorting and analysis and a wide range of other fluorescence-based assays (7, 8). Fluorescent protein probes expressed in vivo, such as *Aequorea victoria* green fluorescent protein and its variants, have proved to be of great value in all fields of cell biology (9). Probes generated by the spontaneous addition of exogenously supplied phycoerythrobilin to recombinant apophytochrome fragments in living cells are also very promising (10). Phycobiliprotein constructs represent a broad array of spectroscopically distinctive proteins with photophysical properties superior to those of probes currently available, and phycobiliprotein subunits have proven highly versatile as fusion partners (11). The expression in prokaryotic or eukaryotic cells of genes encoding enzymes and apo-phycobiliprotein subunit-containing fusion proteins permits intracellular production of constructs carrying specific bilins at unique locations, with broad utility in addressing a variety of questions in cell biology.

SUMMARY OF THE INVENTION

The invention provides recombinant cells which express a fluorescent holo-phycobiliprotein fusion protein and methods of use. Cells which do not naturally express a fluorescent, holo-phycobiliprotein are genetically engineered to comprise a functional pathway for making a fluorescent, holo-phycobiliprotein. The holo-phycobiliprotein fusion proteins comprise a heterologous-to-the-cell, fluorescent, first holo-phycobiliprotein domain fused to a heterologous protein domain. In a particular embodiment, the cell makes and comprises components: a bilin, a recombinant bilin reductase, an apo-phycobiliprotein fusion protein precursor of the fusion protein comprising a corresponding apo-phycobiliprotein domain, and a recombinant phycobiliprotein domain-bilin lyase, which components react inside the cell to form the holo-phycobiliprotein fusion protein.

In a particular embodiment, the cell further comprises a heme and a heme oxygenase which react to form the bilin, particularly a recombinant heme oxygenase such as HO1.

In additional embodiments, the heterologous protein domain is fluorescent and spectroscopically distinguishable from the first holo-phycobiliprotein domain, the heterologous protein domain comprises a heterologous-to-the-cell, fluorescent, second holo-phycobiliprotein domain, the heterologous protein domain comprises a phytochrome domain, the heterologous protein domain comprises a green fluorescent protein (GFP) domain, and/or the fusion protein provides fluorescence resonance energy transfer between the first holo-phycobiliprotein domain and the heterologous protein domain.

The invention may be practiced in a wide variety of cells, including mammalian cells, yeast cells (e.g. *S. cerevisiae*), bacterial cells (e.g. *E. coli*), etc., which may be present in vitro, which are generally isolated from a host, or in situ.

In particularly exemplified applications, (a) the bilin is phycocyanobilin (PCB), the reductase is 3Z-phycocyanobilin:ferredoxin oxidoreductase (PcyA), the apo-phycobiliprotein domain is phycocyanin α subunit domain, and the lyase is heterodimeric phycocyanin α subunit phycocyanobilin lyase (CpcE and CpcF); (b) the bilin is phycocyanobilin (PCB), the reductase is 3Z-phycocyanobilin:ferredoxin oxidoreductase (PcyA), the apo-phycobiliprotein domain is phycoerythrocyanin apo-α subunit domain, and the lyase is heterodimeric phycoerythrocyanin α subunit phycoerythrocyanobilin lyase (PecE and PecF), which further catalyzes the isomerization of the bound bilin to phycobiliviolin; and (c) the bilin is phycoerythrobilin (PEB), the reductase is 3Z-phycoerythrobilin:ferredoxin oxidoreductase (PebA and PebB), the apo-phycobiliprotein domain is phycoerythrin apo-α subunit domain, and the lyase is heterodimeric C-phycoerythrin α subunit phycoerythrobilin lyase (CpeY and CpeZ).

The invention also provides methods of making and using the subject cells and fusion proteins. For example, subject methods include making holo-phycobiliprotein fusion proteins by growing the subject recombinant cells under conditions wherein the cells express the holo-phycobiliprotein fusion protein, which methods may further comprise the step of isolating the holo-phycobiliprotein fusion protein, and/or the step of specifically detecting, including detecting the location, movement, interactions, appearance, or catabolism of the holo-phycobiliprotein fusion protein, particularly within the cell.

In another embodiment, the invention provides holo-phycobiliprotein based transcription reporter cells and assays. For example, the invention includes a recombinant cell which conditionally expresses a heterologous-to-the-cell, fluorescent, first holo-phycobiliprotein domain, wherein the cell makes and comprises components: a bilin, a recombinant bilin reductase, an apo-phycobiliprotein domain, and a recombinant phycobiliprotein domain-bilin lyase, wherein at least one of the reductase, apo-phycobiliprotein domain and lyase is expressed upon activation of a targeted transcriptional promoter, whereupon the components react inside the cell to form the holo-phycobiliprotein domain, which provides a reporter for the activation of the promoter.

DETAILED DESCRIPTION OF PARTICULAR EMBODIMENTS OF THE INVENTION

Figure 1:
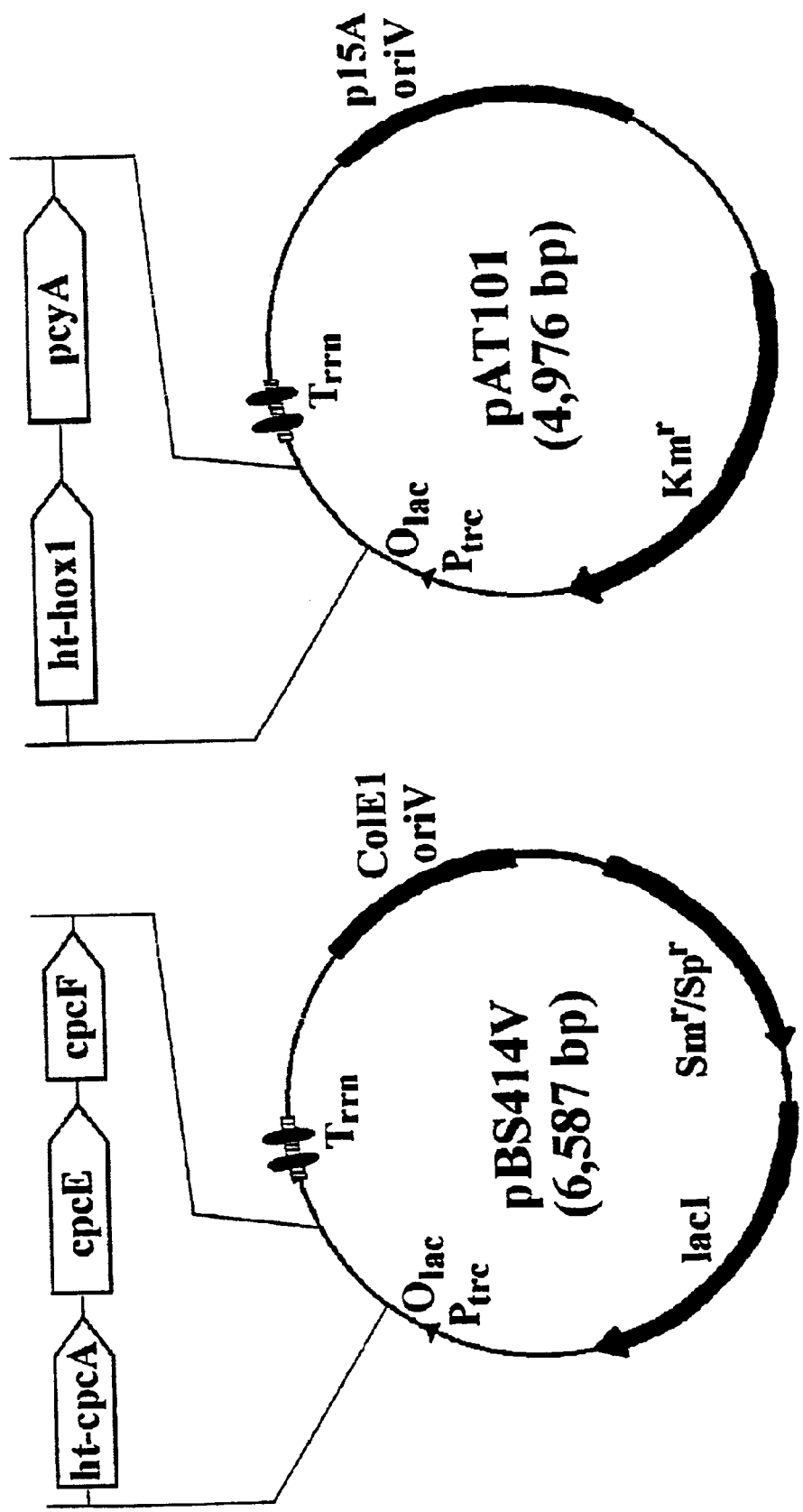
FIG. 1. Physical maps of the pBS414V and pAT101 expression vectors used for in vivo bilin addition to Synechocystis sp. PCC6803 His-tagged phycocyanin apo-α subunit (HT-CpcA) in *E. coli*.

The following descriptions of particular embodiments and examples are offered by way of illustration and not by way of limitation.

The invention provides recombinant cells which express a recombinant, fluorescent holo-phycobiliprotein and methods of use. By recombinant cell is meant that the cell or an ancestor of the cell has been genetically modified to express a protein that is not naturally expressed by the cell or ancestor, i.e. is heterologous to the cell. Similarly, by recombinant protein is meant that the host cell or an ancestor of the cell has been genetically modified to express the protein, which is not naturally expressed by the cell or ancestor, i.e. is heterologous to the cell. Generally, such recombinations are effected by introducing into the cell a foreign genetic construct comprising a coding sequence encoding the protein under the transcriptional control of a promoter, usually a promoter heterologous to the coding sequence. The genetic construct may be integrated into the cellular genome or maintained episomally. Hence, these cells which do not naturally express a fluorescent phycobiliprotein are genetically engineered to comprise a functional biochemical pathway for making a fluorescent phycobiliprotein. In a particular embodiment, the subject cell makes a bilin, a recombinant bilin reductase, a recombinant apo-phycobiliprotein domain, which may be part of a fusion protein, and a recombinant phycobiliprotein domain-bilin lyase, which react inside the cell to form the fluorescent holo-phycobiliprotein domain. The subject lyase catalyzed fluorescent holo-phycobiliproteins are distinct from spontaneously formed adducts, which have inferior fluorescent properties, below.

To make the bilin, the cell generally produces a heme precursor which is subject to a heme oxygenase to form a biliverdin, see e.g. Glazer, 1994, Adv Mol Cell Biol 10, 119–149. The heme oxygenase may be native or recombinant, such as a recombinantly expressed HO1 from Synechocystis sp. PCC6803. The biliverdin is generally further subject to the recombinant bilin reductase and may be further subject to additional enzymes of the cell such as additional reductases, to form the required bilin, which is joined to the required phycobiliprotein domain by the required lyase. However, because biliverdin can form fluorescent adducts with phycobiliproteins and because the tetrapyrrole moiety may be subject to further modification, e.g. isomerization, the term bilin, as used herein, encompasses tetrapyrroles that combine or are already combined with a phycobiliprotein domain to form a fluorescent adduct wherein the tetrapyrrole moiety provides light harvesting, energy transfer functionality to the adduct. Hence, the term encompasses isomeric precursors of the tetrapyrrole moieties of the functional adducts.

A wide variety of recombinant reductases, phycobiliprotein domains, and lyases may be used, and in a wide variety of combinations to obtain a wide variety of recombinant fluorescent phycobiliproteins. For example, any bilin reductase which yields the requisite bilin product sufficient to produce the requisite recombinant fluorescent phycobiliprotein will suffice. For example, copending Ser. No. 09/870, 406, filed May 29, 2001 (PCT/US01/18326, filed Jun. 5, 2001) (Ref. No. UCOO-453-2) describes a large family of suitable HY2 bilin reductases. In particular embodiments, the invention utilizes 3Z-phycocyanobilin:ferredoxin oxidoreductase (PcyA) or 3Z-phycoerythrobilin:ferredoxin oxidoreductase (PebA and PebB). In addition to PcyA, which converts biliverdin to PCB, Frankenberg et al. (6) have described PebA, which converts biliverdin to 15,16-dihydrobiliverdin, and PebB which converts 15,16-dihydrobiliverdin to 3Z-phycoerythrobilin. Similarly, any phycobiliprotein bilin lyase which yields the requisite recombinant fluorescent phycobiliprotein adduct will suffice; noting that the bilin moiety may be subject to further modification to effect or alter fluorescent properties of the ultimate fluorescent phycobiliprotein. The bilin lyases CpcE and CpcF are exemplified in detail below. Suitable bilin lyases with specificities different from CpcE and CpcF include PecE and PecF, which catalyze the addition of PCB to phycoerythrocyanin apo-α subunit and the isomerization of the bound bilin to phycobiliviolin (Jung, et al. (1995) *J. Biol. Chem.* 270, 12877–12884; Zhao, et al.(2000) *FEBS Lett.* 469, 9–13). CpeY plus CpeZ have been reported to catalyze the addition of phycoerythrobilin to one of the bilin attachment sites on the α subunit of C-phycoerythrin (Kahn, et al., (1997) *J. Bacteriol.* 179, 998–1006). The lyase may provide any required isomerase activity, or such activity may be provided by an independent isomerase, which may be endogenous or recombinant.

The required phycobiliprotein domain is similarly limited only by the functional requirement that it be combinable by the lyase with the bilin to form the required fluorescent phycobiliprotein. The phycobiliprotein domain may be expressed independently, or as a fusion protein with a heterologous protein domain (i.e. not naturally fused to the phycobiliprotein domain). Any phycobiliprotein domain having the requisite functionality may be used and these may be derived from natural, semisynthetic or synthetic sequences. A wide variety of natural phycobiliproteins are known in the art, e.g. Apt and Grossman, 1995, J Mol Biol 248, 79–96, including proteins derived from many cyanobacteria, rhodophytes (red algae) and cryptomonads, etc. (see, e.g. Glazer, 1994, J Appl Phycol 6, 105–112; Glazer et al. 1995, Photosynth Res 46, 93–105), particularly phycoerythrins, phycocyanins, and allophycocyanins. In addition, a wide variety of methods are known for modifying such natural sequences to generate semi-synthetics, e.g. Glazer, 1994, supra, describes phycobiliproteins having non-natural, predetermined bilin compositions, and Toole et al., 1998, Mol Micro 30, 475–486 describes recombinations of phycobiliprotein deletion mutants. Finally, known phycobiliprotein structure-function relationships (e.g. Anderson et al., 1998, Mol Micro 30, 467–474) are exploited to generate synthetic sequence analogs using conventional methods.

In a particular embodiment, the phycobiliprotein domain is characterizable as an α or β subunit, based on its sequence similarity to natural α and β phycobiliprotein subunits. The selection of phycobiliprotein domains may yield different results, affecting the heterologous protein domain and/or any additional phycobiliprotein domain, and such differences guide the selection of the carrier phycobiliprotein subunit. For example, the phycocyanin a subunit and the β-L11-α subunit-fusion are preferred when the heterologous protein domain of interest is fused to (displayed on) the N-terminus of the phycobiliprotein domain because of the higher yield and the better spectroscopic properties of the resulting fusion protein. For coupling a heterologous protein domain to the C-terminus of a phycobiliprotein domain, phycocyanin β subunit is better suited because the phycocyanin α subunit is sensitive to extension on its C-terminus (usually leading to incomplete bilin addition and in some instances partial unfolding of the protein).

The phycobiliprotein domain confers fluorescence on the fusion protein, preferably providing fluorescence quantum yield and molar extinction coefficients at least 1%, preferably at least 10%, more preferably at least 50%, more preferably at least 75%, more preferably at least 90% and most preferably substantially equivalent to that of a corresponding unfused phycobiliprotein, measured as described herein. Preferred domains provide extinction coefficients of at least 100K, preferably at least 300K, more preferably at least 1M and/or quantum yields of at least 0.25, preferably at least 0.5, more preferably at least 0.6, as described herein. In other preferred aspects of this embodiment, the fluorescence emission spectrum of the fusion protein is substantially equivalent to that of a corresponding unfused phycobiliprotein.

The phycobiliprotein domain comprises one or more bilins, preferably a plurality of functional bilins contributing to the visible absorption spectrum of the phycobiliprotein domain and fusion protein, preferably natural bilins. The bilins are generally covalently coupled to the phycobiliprotein domain through cysteine thioether linkages, preferably at natural bilin attachment sites. Hence, the phycobiliprotein domain of the fusion protein provides a substrate for enzymatic bilin addition, which may provide natural or non-natural bound bilin distribution, preferably a substrate for enzymes which naturally modify a corresponding natural phycobiliprotein.

The heterologous protein domain of the fusion may be any polypeptide having a requisite functionality and being compatible with that of the phycobiliprotein domain and with assembly of the fusion protein in a functional oligomeric phycobiliprotein. Accordingly, a wide range of displayed domains may be used including domains comprising an affinity tag, an oligomerization moiety, a specific binding moiety and/or a signaling moiety, and including polypeptides which may be coupled to phycobiliproteins by chemical conjugation invention (see, inter alia, U.S. Pat. Nos. 4,520,110; 4,542,104; 4,857,474; 5,055,556; 5,707,804; 5,728,528; and 5,869,255).

The fusion partner may be a displayed domain as described in copending Ser. No. 09/469,194, filed Dec. 21, 1999 (PCT/US00/35028, filed Dec. 21, 2000) (Ref. No. B00-016), preferably of length and sequence sufficient to provide a constrained structure, including at least secondary structure, preferably tertiary structure. In a particular embodiment, the constrained structure is of complexity sufficient to require complex folding and is poorly expressed independent of the fusion protein in active form in conventional expression systems, particularly conventional yeast (e.g. S. cerevisiae) and bacterial (e.g. E. coli) expression systems. Preferred displayed domains are refractive to expression when expressed independent of the fusion proteins, i.e. substantially not expressed in active form, in conventional expression systems, particularly E. coli. The displayed domain may have any spectrophotometric properties compatible with the requisite functionalities of the fusion protein. In a particular embodiment, the displayed domain is substantially transparent to the wavelengths of visible light absorbed by phycobiliproteins, and therefore does not substantially affect the fusion protein and/or oligomeric phycobiliprotein light-harvesting function, and/or is substantially transparent to the wavelength(s) of energy emitted by the phycobiliprotein domain, and therefore is not substantially affected by such energy.

The fusion partner or displayed domain may frequently be displayed on either terminus of the phycobiliprotein domain—important because many proteins preferentially tolerate extension on one of their termini. Preferred expression orientation is readily determined empirically, and in many cases (e.g. for making phycobiliprotein-labeled fluorescent reagents) is advised by published C- and N-terminal GFP fusions. In particular embodiments, display on the N-terminus of a phycobiliprotein β subunit, rather than the α subunit, is more conducive to folding of certain displayed proteins. Use of the subunit-fusion phycocyanins α-L11-β and β-L11-α as the carrier protein may also have certain advantages: the fusion proteins tend to be more stable, and the 1:1 stoichiometry of α and β subunits is ensured.

The fusion proteins may comprise additional components as desired, which may provide modules of functionalities, such as affinity handles, dimer- or oligomerization domains, stabilization domains, specificity domains, signaling domains, etc., apart from any such functionality or functionalities provided by the displayed domain. For example, for constructs to be used as fluorescent labels, introduction of GCN oligomerization domains enhances both the spectroscopic value (more chromophores) and binding affinity (more sites for intermolecular interaction).

Accordingly, the heterologous protein domain may be a target protein to be labeled or traced, a second labeled domain such as a second fluorescent domain, which may be provided by a different phycobiliprotein domain, a phytochrome domain, a GFP domain, etc., etc. In a particular embodiment, the heterologous protein domain is fluorescent and spectroscopically distinguishable from the fluorescent, first holo-phycobiliprotein domain, particularly wherein the fusion protein provides fluorescence resonance energy transfer between the fluorescent first holo-phycobiliprotein domain and the heterologous protein domain.

Hence, a fusion may contain inter alia two phycobiliprotein domains, e.g., CpcA-PecA (a fusion of the α subunit of C-phycocyanin to the α subunit of phycoerythocyanin). The phycocyanin α subunit phycocyanobilin lyase (CpcE+CpcF) adds PCB to the CpcA subunit, whereas the phycoerythrocyanin α subunit phycobiliviolin lyase adds PCB to the PecA subunit and then isomerizes the added bilin to phycobiliviolin (abbreviated PXB). In this construct, PXB is spectroscopically distinguishable from PCB, and the energy absorbed by PXB is quantitatively transferred to PCB. If we also express a fusion with PecA alone, we will have two spectroscopically distinguishable labels in the same cell. Note that this is made possible by the distinctive specificities of the two lyases and the presence of two different phycobiliprotein domains within the same construct.

Analogously, where an apo-phytochrome domain-XXXX domain-PecA fusion is expressed in a cell expressing Hox1, PcyA, PecE, and PecF, there is spontaneous addition of PCB to the apophytochrome domain and phycobiliviolin addition to the PecA domain. The PCB-phytochrome domain adduct is non-fluorescent and quenches the PXB fluorescence from the PXB on the PecA domain. Consequently, the fluorescence signals from such a construct "report" events that change the structure or conformation on the interposing XXXX domain. Cleavage of the XXXX domain eliminates the quenching and results in strong enahancement of the PXB emission from the PecA domain.

In other particular embodiments, the fusion protein comprises a specific binding moiety comprising at least one of a specific binding pair, such as a receptor—ligand pair, e.g. an immunoglobulin antigen-binding domain or antigenic domain, a lectin saccharide-binding domain or glycosylated or glycosylatable domain, an avidin or streptavidin biotin-binding domain or biotinylated or biotinylatable (i.e. providing a substrate for enzymatic biotinylation) domain, etc. In a particular embodiment, the fusion protein comprises a biotinylated or biotinylatable domain, which is preferably biotinylated in the expression system (e.g. cell) selected for expression of the fusion protein. A wide variety of synthetic, semi-synthetic and natural such domains are known in the art, see e.g., Schatz et al. 1993, Bio/Technology 11, 1138–1143; Tatsumi et al., 1996, Anal Biochem 243, 176–180; Samols et al. 1988, J Biol Chem 263, 6461–6464, including homologs in phycobiliprotein producing cyanobacteria, e.g. Gomicki et al. 1993, J Bacteriol 175, 5268–5272; Phung et al., GenBank Accession No. U59235; Nakamura et al. 1998 Nucl Acids Res 26, 63–67. In fact, enzymes sufficient to biotinylate biotinylatable domains have been characterized (e.g. Beckett et al. 1999, Protein Sci 8, 921–929; Buoncristiani et al. 1988, J Biol Chem 263, 1013–1016), permitting in vitro biotinylation (e.g. Li et al., 1992, J Biol Chem 267, 855–863). These biotinylated domains permit especially convenient affinity purification tags (e.g. Cronan 1990, J Biol Chem 265, 10327–10333) and are useful in the many well developed biotin/avidin applications (e.g. Wilchek and Bayer (ed) 1990, Methods Enzymol 184, Academic Press, NY).

In another example, various spacers or flexible linker peptides providing a variety of functionalities, such as a specific endopeptidase recognition and/or cleavage site, an affinity-purification tag, etc., may be used between the heterologous and phycobiliprotein domains. For example, when displayed C-terminally to the phycobiliprotein domain, a specific protease recognition and cleavage site can be engineered immediately upstream from the heterologous protein domain so, upon cleavage with the protease, the heterologous protein domain can be cleanly released from the fusion protein. This strategy also works for most proteins displayed on the N-terminus of the fusion protein because the functions of most heterologous proteins are not affected by C-terminal extensions several residues long. In situations where such C-terminal extension is highly undesirable, an intein domain (Perler FB, Jan. 1, 2000, Nucleic Acids Res 28, 344–345 "InBase, the Intein Database") can be engineered immediately downstream from the heterologous protein domain. Subsequent excision of intein cleanly releases the displayed domain from the fusion protein.

The linkers may also be used to facilitate display of heterologous protein domains that would otherwise interfere with oligomeric phycobilisome assembly. The length and amino acid sequence requirements of such functionality are readily determined empirically for a given fusion construct. Generally, the linkers are preferably from at least 5, preferably at least 10 residues in length, typically requiring no more than 50, and more often no more than 30 residues. To facilitate an unintrusive orientation, small, flexible residues such as Ala, Gly and Ser are particularly convenient components.

The phycobiliprotein domains or fusion proteins comprising such domains are frequently incorporated in a functional oligomeric phycobiliprotein, see e.g. Glazer, 1994, Adv Mol Cell Biol 10, 119–149, comprising at least an α dimer, preferably an α, β heterodimer. The oligomers, especially when assembled into higher-order structures such as trimers, hexamers, rods and phycobilisomes, constrain one displayed protein from interacting with another. This is particularly useful in producing proteins whose function is (1) harmful to the cell but (2) dependent on the formation of dimer or multimer. In a particular embodiment, the oligomeric fusion phycobiliproteins are structurally substantially identical to those of corresponding natural phycobiliproteins and preferably provide fluorescence quantum yield and molar extinction coefficients at least 1%, preferably at least 10%, more preferably at least 50%, more preferably at least 75%, more preferably at least 90% and most preferably substantially equivalent to those of corresponding natural phycobiliproteins. In other preferred aspects of this embodiment, the fluorescence emission spectrum of the oligomeric fusion phycobiliproteins is substantially equivalent to that of corresponding natural phycobiliproteins.

The invention may be practiced in any of a wide variety of cells compatible with expression of the required recombinant fluorescent phycobiliprotein domain, including mammalian cells, yeast cells (e.g. *S. cerevisieae*), bacterial cells (e.g. *E. coli*), etc., which may be present in vitro, which is generally isolated from a host, or in situ.

The subject methods include methods for making a functional displayed domain, the method comprising the step of combining a polypeptide comprising a displayed domain and a phycobiliprotein domain with a phycobiliprotein subunit under conditions to form a subject fusion protein. In particular embodiments, the methods further comprise prior to the combining step, the step of making the polypeptide by expressing a nucleic acid encoding the polypeptide; and/or after the combining step, the step of separating the functional displayed domain from the functional phycobiliprotein domain. The methods steps may occur intracellularly, e.g. in a cell which is or is a progeny of a natural cell which naturally makes functional phycobiliprotein.

The invention also provides methods of using the subject recombinant cells, including methods for making a fluorescent phycobiliprotein domain by growing a disclosed cell under conditions wherein the cell expresses the fluorescent phycobiliprotein domain, which methods may further comprise the step of isolating the fluorescent phycobiliprotein domain, or the step of detecting location, movement, interactions, appearance, or catabolism of the fluorescent phycobiliprotein domain, heterologous protein domain, or fusion protein thereof, such as within the cell.

In another embodiment, the invention provides holo-phycobiliprotein based transcription reporter cells and assays. For example, the invention includes a recombinant cell which conditionally expresses a heterologous-to-the-cell, fluorescent, first holo-phycobiliprotein domain, which may be expressed independently or as part of a fusion protein as described above. The cell makes and comprises a bilin, a recombinant bilin reductase, an apo-phycobiliprotein domain, and a recombinant phycobiliprotein domain-bilin lyase, wherein at least one of the reductase, apo-phycobiliprotein domain and lyase is expressed upon activation of a targeted transcriptional promoter, whereupon the components react inside the cell to form the holo-phycobiliprotein domain, such that the holo-phycobiliprotein domain provides a reporter for the activation of the promoter. Transcriptional reporter assays are well known in the art The disclosed holo-phycobiliprotein domain expression systems may be incorporated into any of the many well-known transcriptional reporter assays, used with essentially any promoter compatible with the subject cells, and may be substituted for other transcriptional reporters, such as luciferase and galactosidase, to obtain alternative spectroscopic readouts.

EXAMPLES AND DETAILED EXPERIMENTAL PROTOCOLS

In this example, the entire pathway for synthesis of a fluorescent holo-phycobiliprotein subunit from a photosynthetic cyanobacterium (Synechocystis sp. PCC6803) was reconstituted in *Escherichia coli*. Cyanobacterial genes encoding enzymes required for the conversion of heme to the natural chromophore, 3Z-phycocyanobilin, namely, heme oxygenase 1 and 3Z-phycocyanobilin:ferredoxin oxidoreductase, were expressed from a plasmid under control of the hybrid trp-lac (trc) promoter. Genes for the apoprotein (C-phycocyanin α subunit; cpcA) and the heterodimeric lyase (cpcE and cpcF) that catalyze chromophore attachment were expressed from the trc promoter on a second plasmid. Upon induction, recombinant *E. coli* utilized the cellular pool of heme to produce holo-CpcA with spectroscopic properties qualitatively and quantitatively similar to those of the same protein produced endogenously in cyanobacteria. About a third of the apo-CpcA was converted to holo-CpcA. No significant bilin addition took place in a similarly engineered *E. coli* strain that lacks cpcE and cpcF.

Materials. Enzymes for DNA manipulation were obtained from New England Biolabs, Inc. (Beverly, Mass.) and Life Technologies, Inc. (Gaithersburg, Md.), and antibiotics from Sigma Chemical Co. (St. Louis, Mo.). Agar and organic nutrients for Luria-Bertani (LB) medium were obtained from Difco (Detroit, Mich.) and other chemicals from Sigma Chemical Co. or Fisher Scientific (Pittsburgh, Pa.). "Super-flow" $Ni^{2+}$-nitrilotriacetic acid ($Ni^{2+}$-NTA) agarose resin for isolation of His-tagged proteins was purchased from Qiagen, Inc. (Valencia, Calif.).

Cultures and Strains. *Escherichia coli* strain DH5α(Life Technologies, MD) grown in LB medium was used in all experiments. Plasmids conferring resistance to spectinomycin were selected with 100 ug $ml^{-1}$ spectinomycin dihydrochloride, while those conferring resistance to kanamycin were selected with 50 ug $ml^{-1}$ kanamycin sulfate. For expression of $P_{trc}$-controlled genes, isopropyl-β-D-thiogalactoside (IPTG) was added to a final concentration of 0.5 mM to exponentially growing cells. Induced cells were grown for 3.5 h at 37° C. with shaking. Cultures were harvested and pellets were stored at −20° C. until used.

Cloning of relevant Synechocystis sp. PCC6803 genes. Standard procedures were used for most DNA manipulations. Gene sequences were obtained from the Kazusa DNA Research Institute CyanoBase (12, 13) and all accession numbers given below refer to that database. Using primers described below, all genes were amplified from PCC6803 genomic DNA by the polymerase chain reaction (PCR). Fidelity of all PCR generated fragments was verified by direct nucleotide sequencing. A more typical *E. coli* ribosomal binding site was engineered upstream of the cpcE, cpcF, and hox1 ORFs. DNA sequence analysis was performed with the program Editbase (Purdue Research Foundation and USDA/ARS) and predicted amino acid sequences were deduced using Lasergene (DNASTAR Inc., Madison, Wis.).

Cloning of the gene encoding Synechocystis sp. PCC6803 phycocyanin α-subunit. PCR primers were used to amplify the cpcA gene (sll1578). The resulting 0.5 kb product was digested with restriction enzymes, NdeI and EcoRI, and cloned into NdeI- and EcoRI-25 digested cloning vector, pBS350V (described in ref. 11), giving plasmid pBS405V. The CpcA construct expressed from pBS405V consists of CpcA fused at the N-terminus to a 24-amino acid sequence that includes a 6xHis-tag (11).

Cloning of the genes encoding the Synechocystis sp. PCC6803 phycocyanin α subunit phycocyanobilin lyase. PCR primers were used to amplify the cpcE gene (slr1878). The resulting 0.85 kb PCR fragment was digested with restriction enzymes, SalI and NotI, and cloned into SalI- and NotI-digested pBS350V, giving plasmid pBS406V. PCR primers were used to amplify the cpcF gene (sll1051). The resulting 0.7 kb product was digested with restriction enzymes, EagI and BamHI, and cloned into EagI- and BamHI-digested pBS350V, giving plasmid pBS407V.

Cloning of the gene encoding Synechocystis sp. PCC6803 heme oxygenase 1. PCR primers were used to amplify the hox1 gene (sll1184; ref. 14). The resulting 0.8 kb product was digested with restriction enzymes, BamHI and AscI, and cloned into BamHI- and AscI-digested pBS350V, yielding plasmid pBS421V.

Cloning of the gene encoding Synechocystis sp. PCC6803 3Z-phycocyanobilin:ferredoxin oxidoreductase. PCR primers were used to amplify the pcyA gene (slr0116). The resulting 0.8 kb product was digested with restriction enzymes, AscI and SphI, and cloned into the AscI- and SphI-digested pBS350V, giving the plasmid pBS422V.

Design of expression vectors. Two expression vectors were designed, each containing a cassette of two or more Synechocystis sp. PCC6803 genes. The aim was to introduce them together into *E. coli* cells, and thereby produce all of the catalytic functions and components required for the formation of phycocyanin holo-α subunit in vivo. The cassette in one vector, pBS414V, contained cpcA along with cpcE and cpcF, and provides all of the components (apo-CpcA, CpcE and CpcF) known to be both necessary and sufficient for the correct addition of PCB to apo-CpcA (15). The cassette in the other vector, pAT101, contained hox1 and pcyA (6), to provide enzymes required for the conversion of heme to phycocyanobilin (PCB), the proximal precursor to the polypeptide-bound bilin (15). Construction of these cassettes is described below (see also FIG. 1).

Plasmid pBS414V containing the cpcA-cpcE-cpcF cassette. The cpcF gene, as a 0.7 kb BamHI-EagI fragment from pBS407V, was cloned into the BamHI- and EagI-digested pBS405V containing ht-cpcA, giving plasmid pBS412V. Subsequently, the cpcE gene, as a 0.85 kb SalI-NotI fragment from pBS406V, was cloned into the SalI- and NotI-digested pBS412V containing ht-cpcA and cpcF, giving the final cassette plasmid, pBS414V.

Construction of plasmid pAT101 containing the PCB biosynthesis cassette. The hox1 gene, as a 0.7 kb NdeI-AscI fragment from pBS421V, was cloned into the NdeI- and AscI-digested pBS350V, giving plasmid pBS425V. Unlike pBS421V, pBS425V allows for expression of an N-terminal 6xHis-tagged HO1 (HT-HO1) fusion protein. Subsequently, the pcyA gene, as a 0.8 kb AscI-SphI fragment from pBS422V was cloned into the AscI- and SphI-digested pBS425V containing hox1, giving plasmid pBS426V. As noted above, a more typical *E. coli* ribosomal binding site is present upstream of each of the ORFs in this cassette and for the ORFs in plasmid pBS414V.

Since plasmids pBS414V and pBS426V, containing the two distinct gene cassettes, were derived from the same parental pBS350V with the ColE1 origin of replication, they are incompatible within the same *E. coli* cell. In order to maintain and express these two cassettes within the same *E. coli* cell, the use of different but compatible origins of replication was required. To achieve this goal, the 2.2 kb fragment generated from pBS426V by SspI (partial) and BspHI digestion, containing the trc promoter, lac operator, and the genes encoding HO1 and PcyA, was cloned into the 2.77 kb BspHI-(partial) and PsiI-digested plasmid pACYC177 (Genbank Accession No. X06402), which contains the p15A origin of replication (16) and confers resistance to kanamycin. The β-lactamase gene in pACYC177 was completely removed in the cloning. The resulting pACYC177 derivative, pAT101, carries the genes required for PCB synthesis (ht-hox1 andpcyA), and is compatible with pBS414V which carries the genes encoding the heterodimeric phycocyanin α subunit PCB lyase (cpcE and cpcF) and HT-CpcA (ht-cpcA).

As shown in FIG. 1, vector pBS414V carries the phycocyanin α subunit phycocyanobilin lyase genes cpcE and cpcF and ht-cpcA, the gene encoding HT-CpcA. Plasmid pBS414V contains the ColE1 oriV for replication in *E. coli* and the aadA gene conferring resistance to spectinomycin and streptomycin. Expression is controlled by the trc promoter, lac operator, and the lacI$^q$ gene encoding the Lac repressor. Two strong, bidirectional, r-independent transcriptional terminator structures from the *E. coli* rrnB gene are located downstream of the expression cassette. Vector pAT101 expresses the genes involved in phycocyanobilin biosynthesis from heme: the heme oxygenase 1 (hox1) and 3-Zphycocyanobilin:ferredoxin oxidoreductase (pcyA). Plasmid pAT101 contains the p15A oriV for replication in *E. coli* and the kanamycin resistance gene. The use of compatible origins of replication and different selectable markers allows for both plasmids to be maintained within the same *E. coli* cell. Expression of the genes carried by pAT101 is under the same control elements as in pBS414V. Plasmid pBS405V (herein) was equivalent to plasmid pBS414V, except that the insert contained only ht-cpcA.

Isolation of His-tagged proteins by immobilized metal affinity chromatography. Cell pellets were thawed and resuspended in 20 ml of cold (0–4° C.) buffer 0 (20 mM Tris-HCl, pH 8.0, 50 mM NaCl, 50 mM KCl). Phenylmethylsulfonylfluoride and β-mercaptoethanol were added to final concentrations of 1 mM and 10 mM, respectively, immediately before breakage of cells by passage through a French pressure cell three times at 18,000 psi. Cell debris was removed by centrifugation at 4° C. in a Beckman JA20 rotor at 30,000×g for 1 h.

The supernatant solution was mixed with 2–3 ml of Ni$^{2+}$-NTA resin at 4° C. for 15 min before the resin was loaded onto a column. The resin was then washed with 10 column volumes each of cold buffer A1 (20 mM Tris-HCl, pH 8.0, 50 mM NaCl, 50 mM KCl, 20 mM imidazole, 5% v/v glycerol), buffer B (20 mM Tris-HCl, pH 8.0, 500 mM NaCl, 500 mM KCl), and buffer A2 (20 mM Tris-HCl, pH 8.0, 50 mM NaCl, 50 mM KCl, 30 mM imidazole). His-tagged proteins were eluted from the resin with buffer C (20 mM Tris-HCl, pH 8.0, 50 mM NaCl, 50 mM KCl, 200 mM imidazole) and were then dialyzed overnight against 50 mM Na-phosphate pH 7.0.

Absorbance and fluorescence spectrometry. Absorbance spectra were acquired on a computer-controlled, dual-beam λ6 UV/VIS spectrophotometer (Perkin-Elmer Corp., Norwalk, Conn.). Corrected fluorescence spectra were obtained on a FP-750 spectrofluorometer (Jasco Inc., Easton, Md.). Excitation and emission slits were set at 5 nm for all measurements.

A minimal biosynthetic pathway in cyanobacteria leading from heme to the formation of the cysteinyl adduct of PCB with CpcA (FIG. 2) is consistent with substantial in vivo and in vitro data (4, 6, 14, 15, 17–21).

Figure 2:
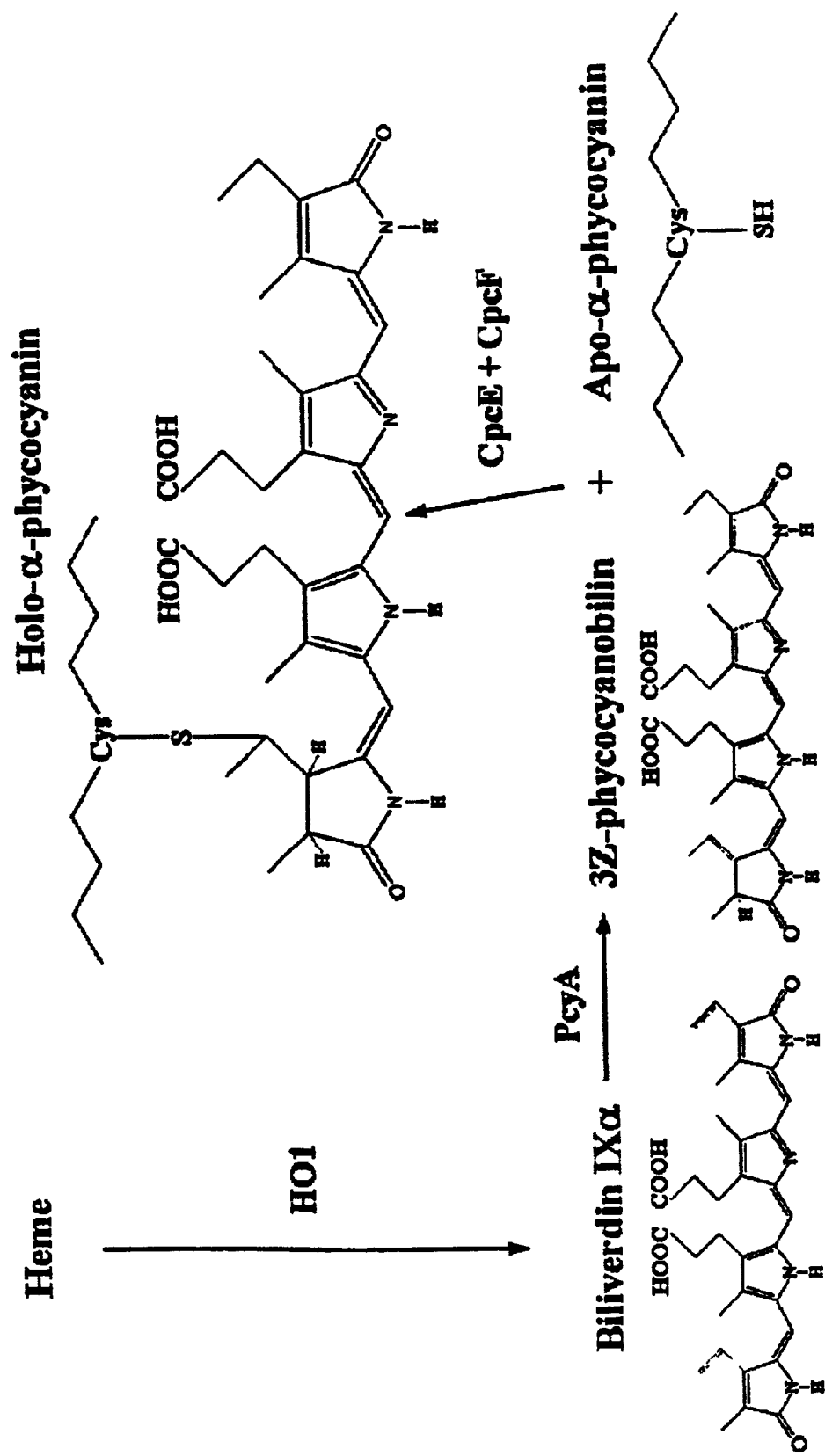
FIG. 2. Minimal biosynthetic pathway for the production of phycocyanobilin from heme, and its addition to the C-phycocyanin apo-α subunit.

To test the predictions of this scheme, two strains of *E. coli*, each carrying two expression vectors, were generated. To maintain both plasmids simultaneously, double transformants were selected for resistance to both spectinomycin (Sp) and kanamycin (Km), and were grown with both Sp and Km. *E. coli* strain DH5α(414V,101) carries plasmids pBS414V (ht-cpcA-cpcE-cpcF cassette, Sp$^r$) and pAT101 (ht-hox1-pcyA cassette, Km), and expresses all the known genes believed to be involved in PCB biosynthesis and its addition to apo-CpcA (FIG. 2). The other *E. coli* strain, DH5α(405V,101), carries plasmid pBS405V (expressing CpcA but lacking CpcE and CpcF, Sp$^r$) and plasmid pAT101. Comparison of the properties of the His-tagged CpcA proteins recovered from these two *E. coli* strains tests the stringency of the requirement for CpcE and CpcF for PCB addition in vivo. Previous studies have shown that the HT-CpcA behaves just like untagged CpcA in cyanobacteria (11).

Expression of the gene cassettes in these two strains of *E. coli* led to two very different phenotypes. Upon induction with IPTG, the *E. coli* strain DH5α(414V,101) culture acquired a pronounced blue tint. This color change was not seen in the culture of DH5α(405V,101). HT-CpcA was purified from strain DH5α(414V,101) by affinity chromatography. Analysis of Coomassie-stained gels after SDS-PAGE of the purified protein showed two distinct bands in a ratio of ~1:2, of 21.1 kDa (band a) and 20.5 kDa (band b), corresponding to the calculated molecular weights of His-tagged holo- and apo-CpcA, respectively. Upon exposure to Zn$^{2+}$ (22) and UW illumination, only band a was fluorescent, indicating that it contained covalently attached bilin.

The ratio of bands a:b was unaltered in HT-CpcA preparations from DH5α(414V,101) cultures grown in medium supplemented with 5 mM δ-aminolevulinic acid (a precursor of heme biosynthesis), with 0.5 uM ferric ammonium citrate (enhances heme biosynthesis in *E. coli*), or with both. The yield of holo-HT-CpcA, calculated from the 625 nm ($\epsilon_M$ 127,600 M$^{-1}$ cm$^{-1}$; see below) absorbance was ~0.4 mg per gram wet weight of *E. coli* cells.

Figure 3:
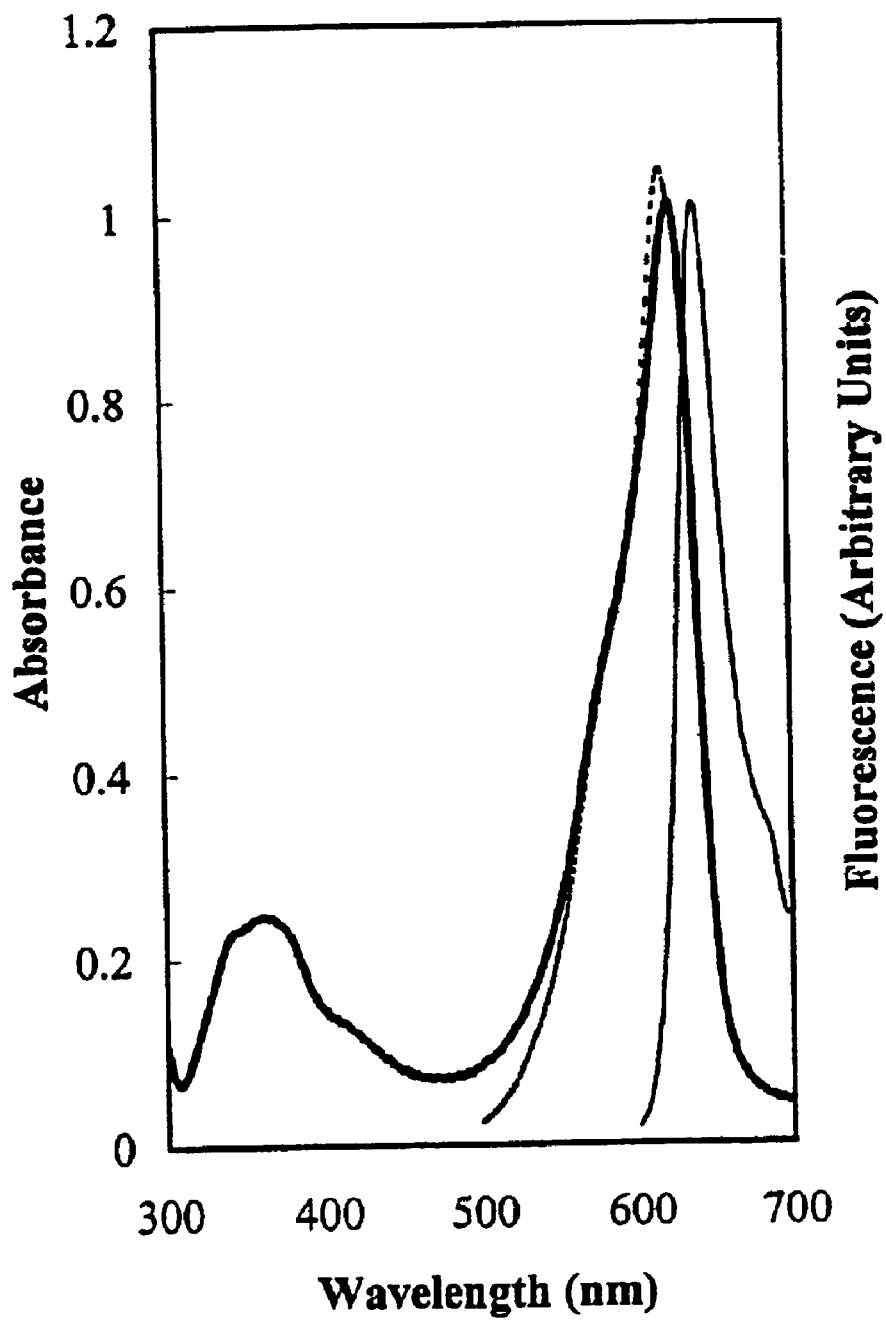
FIG. 3. Spectroscopic properties of Synechocystis sp. PCC6803 holo-HT-CpcA expressed in *E. coli*. Shown are the absorbance ($\lambda_{max}$ 625 nm; thick solid line), fluorescence emission ($\lambda_{max}$ 641 nm; $\lambda_{exc}$ 580 nm; thin solid line), and fluorescence excitation ($\lambda_{exc}$ 645 nm; fluorescence $\lambda_{max}$ 619 nm; dashed line) spectra for HT-CpcA purified from *E. coli* by affinity chromatography. The fluorescence excitation spectrum was normalized to the absorbance spectrum at 625 nm.

Since apo-HT-CpcA does not absorb light above 320 nm, the spectroscopic properties of the holo-HT-CpcA were determined without fractionation of the apo- and holo-HT-CpcA mixture. The absorbance spectrum of the holo-HT-CpcA had a $\lambda_{max}$ at 625 nm and a ratio of $A_{625}$ nm:$A_{369}$ nm of 4.14 (FIG. 3). The corresponding values for Synechococcus sp. PCC7002 holo-CpcA are 620 nm and 4.22 (see FIG. 3 in ref. 5). The $\lambda_{max}$ for Anabaena sp. PCC7120 holo-HT-CpcA is at 622 nm with $\epsilon M$ 109,000 M$^{-1}$ cm$^{-1}$. The absorbance properties of native holo-CpcA preparations from other cyanobacteria are similar (e.g., ref. 23). The holo-HT-CpcA produced in *E. coli*, denatured in 8M urea at pH 2, had a $\lambda_{max}$ 661 nm and a ratio of $A_{352}$ nm:$A_{661}$ nm of 1.03, values characteristic of polypeptide-bound PCB in the denatured cyanobacterial C-phycocyanin α subunit (24). From the acid urea spectrum, an $\epsilon M$ of 127,600 M$^{-1}$ cm$^{-1}$ at 625 m in 50 mM Na-phosphate, pH 7, was calculated for the native holo-HT-CpcA. The fluorescence emission maximum of the holo-HT-CpcA produced in *E. coli* was at 641 nm (FIG. 3), as compared to 642 nm for Synechococcus sp. PCC7002 holo-CpcA (12), and 637 nm for Anabaena sp. PCC7120 holo-HT-CpcA. The excitation spectrum of the holo-HT-CpcA produced in *E. coli* corresponded well to the absorbance spectrum (see FIG. 3), indicating that only one red fluorescence-emitting species was present. The absorbance spectrum was determined at a holo-HT-CpcA concentration of $9.2 \times 10^{-6}$ M, whereas the excitation spectrum was measured at $4.6 \times 10^{-7}$ M; the small red shift in the peak of the absorbance spectrum relative to that of the excitation spectrum reflects the concentration-dependent red shift that accompanies dimerization of holo-CpcA (24). The fluorescence quantum yield of holo-HT-CpcA produced in *E. coli* was 0.31, as compared to 0.23 for Anabaena sp. PCC7120 holo-HT-CpcA.

Upon induction, DH5α(405V,101) expressed a similar level of HT-CpcA as did DH5α(414V,101). SDS-PAGE analysis of HT-CpcA purified from DH5α(405V,101) showed a single major band with a molecular weight corresponding to apo-HT-CpcA, and exposure of the gel to UV illumination after exposure to $Zn^{2+}$ indicated the complete absence of any fluorescent bands. When ten times as much protein was loaded on the gel, a very weak fluorescence was detected in the corresponding band. Spectroscopic analysis of affinity-purified HT-CpcA fraction from DH5α(405V, 101) indicated an upper limit of <1% to any bilin-bearing CpcA in the preparation.

The disclosed methods for expressing fluorescent phycobiliproteins in cells which do not naturally express such proteins are indeed remarkable. Our prior studies with yeast expressing CpcA, CpcE, and CpcF, showed that even though soluble and active proteins were produced, no holo-CpcA formed upon PCB addition to the cells under a wide variety of conditions (25). In contrast, our present in vivo results show that the introduced recombinant constructs are sufficient to create a functional pathway for fluorescent phycobiliprotein production and that there are not additional requirements nor inhibitors present in vivo. Furthermore, our results demonstrate that in contrast to our in vitro results, in vivo expression effects sufficient bilin synthesis to meet the Km of the required lyase reaction.

1. Glazer, A. N. (1994) in *Advances in Molecular and Cell Biology*, ed. Bittar, E. E. & Barber, J. (JAI, Greenwich), pp. 119–149.
2. Sidler, W. A. (1994) in *The Molecular Biology of Cyanobacteria*, ed. Bryant, D. A. (Kluwer, Dordrecht), pp. 139–216.
3. Glazer, A. N. (1988) *Methods Enzymol.* 167, 291–303.
4. Beale, S. I. (1984)) in *The Molecular Biology of Cyanobacteria*, ed. Bryant, D. A. (Kluwer, Dordrecht), pp. 519–558.
5. Fairchild, C. D. and Glazer, A. N. (1994) *J. Biol. Chem.* 269, 8686–8694.
6. Frankenberg, N., Mukougawa, K., Kohchi, T., and Lagarias, J. C. (2001) *The Plant Cell* 13, 965–972.
7. Oi, V. T., Glazer, A. N., and Stryer, L. (1982) *J. Cell Biol.* 93, 981–986.
8. Glazer. A. N. (1999) in *Chemicals from Microalgae*, ed. Cohen, Z. (Taylor & Francis, London), pp. 261–280.
9. Heim, R. and Tsien, R. Y. (1996) *Curr. Biol.* 6, 178–182.
10. Murphy, J. T. and Lagarias, J. C. (1997) *Curr. Biol.* 7, 870–876.
11. Cai, Y. A., Murphy, J. T., Wedemayer, G. J., and Glazer, A. N. (2001) *Anal. Biochem.* 290, 186–204.
12. Nakamura, Y., Kaneko, T., Hirosawa, M., Miyajima, N., and Tabata, S. (1998) *Nucleic Acids Res.* 26, 63–67.
13. Nakamura, Y., Kaneko, T., and Tabata, S. (2000) *Nucleic Acids Res.* 28, 72.
14. Cornejo, J., Willows, R. D., and Beale, S. I. (1998) *Plant J.* 15, 99–107.
15. Fairchild, C. D., Zhao, J., Zhou, J., Colson, S. E., Bryant, D. A., and Glazer, A. N. (1982) *Proc. Natl. Acad. Sci. USA* 89, 7017–7021.
16. Sambrook, J., Fritsch, E. F., and Maniatis, T. (1989) *Molecular Cloning. A Laboratory Manual*. (Cold Spring Harbor Laboratory, New York), $2^{nd}$ Ed., Sect. 1.3, pp.3–5.
17. Zhou, J., Gasparich, G. E., Stirewalt, V. L., De Lorimier, R., and Bryant, D. A. (1992) *J. Biol. Chem.* 267, 16138–16145.
18. Swanson, R. V., Zhou, J., Leary, J. A., Williams, T., De Lorimier, R., Bryant, D. A., and Glazer, A. N. (1992) *J. Biol. Chem.* 267, 16146–16154.
19. Cai, Y. A., Schwartz, S. H., and Glazer, A. N. (1997) *Photosynthesis Res.* 53, 109–120.
20. Arciero, D. M., Bryant, D. A., and Glazer, A. N. (1988) *J. Biol. Chem.* 263, 18343–18349.
21. Arciero, D. M., Dallas, J. L., and Glazer, A. N. (1988) *J. Biol. Chem.* 263, 18350–18357.
22. Berkelman, T. R. and Lagarias, J. C. (1986) *Anal Biochem.* 156, 194–201.
23. Glazer, A. N., Fang, S., and Brown, D. M. (1973) *J Biol. Chem.* 248, 5679–5685.
24. Glazer, A. N. and Fang S. (1973) *J. Biol. Chem.* 248, 659–662.
25. Schroeder, B. G. (1997) *Doctoral dissertation*, University of California, Berkeley.

All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A recombinant cell which expresses a holo-phycobiliprotein fusion protein comprising a heterologous-to-the-cell, fluorescent, holo-phycobiliprotein domain fused to a heterologous protein domain, wherein the cell makes and comprises components: a bilin, a recombinant bilin reductase, an apo-phycobiliprotein fusion protein precursor of the fusion protein comprising a corresponding apo-phycobiliprotein domain, and a recombinant phycobiliprotein domain-bilin lyase, which components react inside the cell to form the holo-phycobiliprotein fusion protein.

2. The cell of claim 1, wherein the cell further comprises a heme and a heme oxygenase which react to form the bilin.

3. The cell of claim 1, wherein the cell further comprises a heme and a recombinant heme oxygenase which react to form the bilin.

4. The cell of claim 1, wherein the cell further comprises a heme and a recombinant heme oxygenase which react to form the bilin, and the recombinant heme oxygenase is HO1.

5. The cell of claim 1, wherein the heterologous protein domain is fluorescent and spectroscopically distinguishable from the holo-phycobiliprotein domain.

6. The cell of claim 1, wherein the heterologous protein domain is fluorescent and spectroscopically distinguishable from the holo-phycobiliprotein domain, and the heterologous protein domain comprises a heterologous-to-the-cell, fluorescent, second halo-hycobiliprotein domain.

7. The cell of claim 1, wherein the heterologous protein domain is fluorescent and spectroscopically distinguishable from the holo-phycobiliprotein domain, and the heterologous protein domain comprises a phytochrome domain.

8. The cell of claim 1, wherein the heterologous protein domain is fluorescent and spectroscopically distinguishable from holo-phycobiliprotein domain, and the heterologous protein domain comprises a green fluorescent protein (GFP) domain.

9. The cell of claim 1, wherein the heterologous protein domain is fluorescent and spectroscopically distinguishable from the holo-phycobiliprotein domain, and the fusion protein provides fluorescence resonance energy transfer between the first holo-phycobiliprotein domain and the heterologous protein domain.

10. The cell of claim 1, wherein the cell is a mammalian cell.

11. The cell of claim 1, wherein the cell is a yeast cell.

12. The cell of claim 1, wherein the cell is a bacterial cell.

13. The cell of claim 1, wherein the cell is an Escherichia coli cell.

14. The cell of claim 1, wherein the cell is in situ.

15. The cell of claim 1, wherein the bum is phycocyanobilin (PCB), the reductase is 3Z-phycocyanobilin:ferredoxin oxidoreductase (PcyA), the apo-phycobiliprotein domain is phycocyanin α subunit domain, and the lyase is heterodimeric phycocyanin α subunit phycocyanobilin lyase (CpcE and CpcF).

16. The cell of claim 1, wherein the bilin is phycocyanobilin (PCB) the reductase is 3Z-phycocyanobilin:ferredoxin oxidoreductase (PcyA), the apo-phycobiliprotein domain is phycoerythrocyanin apo-α subunit domain, and the lyase is heterodimeric phycoerythrocyanin α subunit phycoerythrocyanobilin lyase (PecE and PecF), which further catalyzes the isomerization of the bum to phycobiliviolin.

17. The cell of claim 1, wherein the bum is phycocrythrobilin (PEB), the reductase is 3Z-phycoerythrobilin:ferredoxin oxidoreductase (PebA and PebB), the apo-phycobiliprotein domain is phycoerythrin apo-α subunit domain, and the lyase is heterodimeric C-phycoerythrin α subunit phycoerythrobilin lyase (CpeY and CpeZ).

* * * * *

UNITED STATES PATENT AND TRADEMARK OFFICE
CERTIFICATE OF CORRECTION

PATENT NO. : 6,740,507 B2
DATED : May 25, 2004
INVENTOR(S) : Alexander N. Glazer, Aaron J. Tooley and Yuping Cai It is certified that error appears in the above-identified patent and that said Letters Patent is hereby corrected as shown below:

Title page,
After Item [57], ABSTRACT, "17 Claims" should read -- 20 Claims --

Column 15,
Line 16, "the first" should read -- the --;

Column 16,
Line 1, claim 14 should be canceled.
Lines 2, 14 and 15, "the bum" should read -- the bilin --.
Claims 15, 16 and 17 should be renumbered to 14, 15 and 16 respectively.
Line 22, please insert the following claims:
17. A method for making a holo-phycobiliprotein fusion protein, comprising growing the cell of claim 1 under conditions wherein the cell expresses the holo-phycobiliprotein fusion protein.
18. The method of claim 17, further comprising the step of isolating the holo-phycobiliprotein fusion protein.
19. The method of claim 17, further comprising the step of specifically detecting the holo-phycobiliprotein fusion protein.
20. The method of claim 17, further comprising the step of specifically detecting the holo-phycobiliprotein fusion protein within the cell.

Signed and Sealed this

Nineteenth Day of April, 2005

JON W. DUDAS
*Director of the United States Patent and Trademark Office*